US011439137B2

(12) United States Patent
Jackson

(10) Patent No.: US 11,439,137 B2
(45) Date of Patent: Sep. 13, 2022

(54) AUTOMOBILE HIGH-TEMPERATURE PEST EXTERMINATION DEVICE

(71) Applicant: KABUSHIKI KAISHA NIHON YUSHUTSU JIDOUSHA KENSA CENTER, Yokohama (JP)

(72) Inventor: Damon Scott Jackson, Yokohama (JP)

(73) Assignee: KABUSHIKI KAISHA NIHON YUSHUTSU JIDOUSHA KENSA CENTER, Kanagawa-ken (JP)

( * ) Notice: Subject to any disclaimer, the term of this patent is extended or adjusted under 35 U.S.C. 154(b) by 389 days.

(21) Appl. No.: 16/355,619

(22) Filed: Mar. 15, 2019

(65) Prior Publication Data
US 2020/0000080 A1 Jan. 2, 2020

(30) Foreign Application Priority Data

Jun. 29, 2018 (JP) .............................. JP2018-124966
Sep. 20, 2018 (JP) .............................. JP2018-176409

(51) Int. Cl.
*A01M 1/20* (2006.01)
(52) U.S. Cl.
CPC ..... *A01M 1/2094* (2013.01); *A01M 2200/011* (2013.01)
(58) Field of Classification Search
CPC .......... A01M 1/2094; A01M 2200/011; A01M 1/20; A01M 17/00; A01M 19/00
USPC ................. 34/543, 546, 549, 552, 553, 554; 432/120, 199; 392/347, 349, 350, 360, 392/361, 354, 355, 356; 219/285, 400; 43/144
See application file for complete search history.

(56) References Cited

U.S. PATENT DOCUMENTS

| | | | | |
|---|---|---|---|---|
| 1,940,948 A | * | 12/1933 | Harsch ................... | C21D 1/767 432/9 |
| 3,422,465 A | * | 1/1969 | Jones ..................... | A61H 33/06 4/532 |
| 4,395,233 A | * | 7/1983 | Smith ..................... | F26B 21/02 126/21 A |
| RE31,765 E | * | 12/1984 | Guibert .................. | A23L 3/365 126/21 A |
| 5,696,872 A | * | 12/1997 | Seward .................. | F24C 15/322 392/341 |
| 8,635,995 B2 | * | 1/2014 | Kuhne ................... | F24C 15/322 126/21 A |

(Continued)

FOREIGN PATENT DOCUMENTS

JP 2003-267803 A 9/2003
WO WO-2013111336 A1 * 8/2013 .......... A01M 1/2094

*Primary Examiner* — Darren W Ark
*Assistant Examiner* — Zoe Tam Tran
(74) *Attorney, Agent, or Firm* — Cheng Law Group, PLLC

(57) ABSTRACT

A device for applying, for a predetermined interval, heated air, which is heated to a pest extermination temperature to a to-be-treated automobile, which is housed in a freely accessible manner in a treatment chamber to exterminate pests inside the automobile includes a circulation fan device arranged in the treatment chamber, a suction part of which is oriented toward the inside of the treatment chamber, a heating member mounted in a discharge part of the circulation fan device, and a rectification member for adjusting the flow direction of the heated air delivered into the chamber via the heating member.

13 Claims, 5 Drawing Sheets

(56) References Cited

U.S. PATENT DOCUMENTS

| | | | | |
|---|---|---|---|---|
| 2001/0004069 A1* | 6/2001 | Kim | H05B 6/6473 | 219/400 |
| 2002/0088790 A1* | 7/2002 | Nolan | H05B 6/6485 | 219/400 |
| 2004/0163635 A1* | 8/2004 | Thorneywork | H05B 6/6405 | 126/21 A |
| 2005/0108920 A1* | 5/2005 | Takenoshita | A01M 1/2094 | 43/132.1 |
| 2009/0045184 A1* | 2/2009 | Nam | F24C 15/322 | 219/400 |
| 2009/0134140 A1* | 5/2009 | Van Der Weij | A47J 37/0641 | 219/400 |
| 2010/0311318 A1* | 12/2010 | Hause | F04D 27/004 | 454/256 |
| 2011/0162228 A1* | 7/2011 | Park | D06F 58/30 | 34/427 |
| 2013/0269239 A1* | 10/2013 | Whitley | A01M 1/2094 | 43/132.1 |
| 2014/0083992 A1* | 3/2014 | Linnewiel | A21B 3/04 | 219/400 |
| 2015/0052800 A1* | 2/2015 | Timbrook, Jr. | A01M 1/2094 | 43/132.1 |
| 2016/0249598 A1* | 9/2016 | Savino | B08B 1/00 | 134/105 |

* cited by examiner

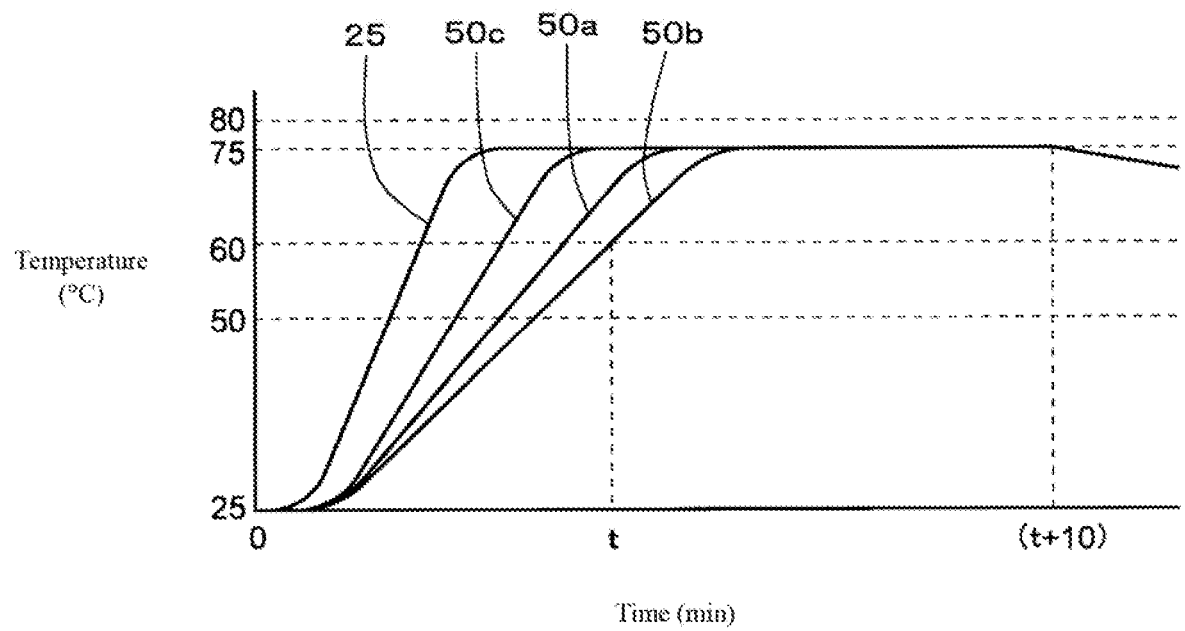

AUTOMOBILE HIGH-TEMPERATURE PEST EXTERMINATION DEVICE

FIELD

The present invention relates to an automobile high-temperature pest extermination device which exterminates pests attached to automobiles by a high-temperature treatment.

BACKGROUND

When exporting goods, if insects or the like native to the country of export are attached to the export goods, transportation vessel, etc., problems such as adverse impact on the ecosystem of the destination country by such insects or the like as invasive organisms may occur. In particular, damage to agricultural crops by these types of invasive organisms is serious. Such invasive organisms are treated as pests, and as a result, unloading of the export goods in the export destination country may not be permitted. Thus, strict quarantine of export goods is necessary.

For example, in recent years, in New Zealand, the attachment of brown marmorated stink bugs to automobiles exported from Japan was confirmed. It is known that these stink bugs are difficult to find, extermination thereof is difficult, the bugs' fertility rates are high, etc. In New Zealand, where agriculture is extensive, stinkbugs are of particular interest as pests to be exterminated. As a result, transport vessels that have confirmed that stink bugs have attached thereto have been forced to leave the country, bringing about a deterioration in the export situation of automobiles from Japan.

New Zealand has become a very important automobile export market for Japan since automobiles are not domestically produced. Thus, the deterioration in the export situation of automobiles from Japan not only has a significant impact on the Japanese economy, but it also hurts New Zealand's economy, which depends on the export automobiles from Japan for domestic distribution. Thus, the construction of a means for reliably exterminating pests represented by these stink bugs is an urgent matter.

Generally, when pests are exterminated, fumigation using an agent such as alkyl iodide is performed (refer to, for example, Patent Literature 1). However, since automobiles are precision machines, pest extermination by means of a fumigation agent can adversely affect various components of the automobile, or the fumigation agent may remain in the filter or the like of the air conditioner, which can cause unpleasant odors, which is not preferable.

Furthermore, fumigation treatment takes several days, and costs increase due to the use of the fumigation agent. Thus, in particular in the export of automobiles, in which hundreds of thousands of exported vehicles per year are subjected to treatment, pest extermination by fumigation is too time-consuming and it is necessary to secure an enormous treatment facility in an area having many restrictions, such as a harbor, to facilitate such a large number of automobiles. Appropriate pest extermination of export automobiles thereby is virtually impossible. Thus, there is a need for a new method capable of efficiently and reliably exterminating pests for the treatment of a large number of export automobiles.

CITATION LIST

Patent Literature

[PTL 1] Japanese Unexamined Patent Publication (Kokai) No. 2003-267803

SUMMARY

Technical Problem

The present invention was made in light of these problems and aims to provide an automobile high-temperature pest extermination device which can reduce treatment time, even for a large number of to-be-treated vehicles, and which can efficiently and effectively exterminate pests by a high-temperature treatment without the use of a fumigation agent.

Solution to Problem

The first aspect of the present invention provides an automobile high-temperature pest extermination device, comprising a treatment chamber including an inlet and an outlet, which comprise openable and closable door parts, in which heated air which has been heated to a pest extermination temperature is applied to an enclosed space in which a to-be-treated automobile is self-propelled and accommodated, a circulation fan device arranged in the treatment chamber and including a suction part, a discharge part, and a fan member, the fan member comprising a large propeller fan having a diameter in the range of 1000 mm to 1500 mm and the front side of the fan member being oriented toward the inside of the treatment chamber, the circulation fan device being configured so that air in the treatment chamber is suctioned from the front side thereof via the suction part, and the suctioned air is discharged in both side directions via the discharge part on the rear surface of the fan member, a heating member provided in the discharge part of the circulation fan device to heat discharged air, a rectification member for adjusting, in the horizontal direction, the flow direction of the heated air delivered into the chamber via the heating member, chamber interior temperature detection means for detecting a chamber interior temperature of the treatment chamber, vehicle interior temperature detection means for detecting a vehicle interior temperature of the to-be-treated automobile, and heating temperature control means for controlling a heating temperature of air discharged from the circulation fan device and a treatment time based on the chamber interior temperature detection means and the vehicle interior temperature detection means.

(Deleted).

The second aspect of the present invention provides the automobile high-temperature pest extermination device according to the first aspect of the present invention, wherein a plurality of treatment chambers are connected in series as a connectable treatment unit so as to house a plurality of to-be-treated automobiles therein.

The third aspect of the present invention provides the automobile high-temperature pest extermination device according to the second aspect of the present invention, wherein a plurality of the treatment chambers, which are connected in series, are arranged in parallel rows.

The fourth aspect of the present invention provides the automobile high-temperature pest extermination device according to the second or third aspect of the present invention, comprising a centralized management part for collectively managing the operations of the plurality of treatment chambers.

Advantageous Effects of Invention

According to the automobile high-temperature pest extermination device according to the first aspect of the present invention, since a treatment chamber including an inlet and an outlet, which comprise openable and closable door parts, in which heated air which has been heated to a pest extermination temperature is applied to an enclosed space in which a to-be-treated automobile is self-propelled and accommodated, a circulation fan device arranged in the treatment chamber and including a suction part, a discharge part, and a fan member, the fan member comprising a large propeller fan having a diameter in the range of 1000 mm to 1500 mm and the front side of the fan member being oriented toward the inside of the treatment chamber, the circulation fan device being configured so that air in the treatment chamber is suctioned from the front side thereof via the suction part, and the suctioned air is discharged in both side directions via the discharge part on the rear surface of the fan member, a heating member provided in the discharge parts of the circulation fan device to heat discharged air, a rectification member for adjusting, in the horizontal direction, the flow direction of the heated air delivered into the chamber via the heating member, chamber interior temperature detection means for detecting a chamber interior temperature of the treatment chamber, vehicle interior temperature detection means for detecting a vehicle interior temperature of the to-be-treated automobile, and heating temperature control means for controlling a heating temperature of air discharged from the circulation fan device and a treatment time based on the chamber interior temperature detection means and the vehicle interior temperature detection means are provided, automobile pests can be reliably controlled by a high-temperature treatment without the use of a fumigation agent. Additionally, according to the present invention, by providing a circulation fan device and heating members in the treatment chamber to circulate and distribute heated air, heating unevenness within the chamber is controlled, whereby the treatment chamber can be effectively and efficiently heated while maintaining a substantially uniform heating temperature, and as a result, treatment efficiency can be significantly improved and cost can be reduced.

Furthermore, since the fan member, which is a large propeller fan having a diameter of 1000 mm to 1500 mm, is arranged so that the front surface side thereof faces the interior of the treatment chamber, the air within the chamber can be drawn and discharged at an appropriate air volume and speed. Even for automobiles, which are large treatment targets, the heat treatment temperature can be raised and maintained efficiently, whereby effective heat treatment can be performed and treatment time can be greatly reduced. Due to the rectification member, which adjusts, in the horizontal direction, the flow direction of the heated air delivered into the chamber through the heating members, the heated air can be effectively brought into contact with the interior and exterior of a box-shaped automobile having a floor plate, a roof plate, and an intricate internal structure, and appropriate pest control can be achieved even for a large number of to-be-treated automobiles, whereby appropriate pest control can be performed more efficiently and effectively even for a large number of to-be-treated automobiles.

According to the automobile high-temperature pest extermination device according to the second aspect of the present invention, a plurality of treatment chambers are connected in series as a connectable treatment unit so as to house a plurality of to-be-treated automobiles therein. Thus, since each treatment chamber includes a circulation fan device and heating members for circulating and distributing heated air, even large numbers of various types of to-be-treated automobiles can be efficiently treated and adaptation to the size of the installation location becomes easy, whereby versatility is improved.

According to the automobile high-temperature pest extermination device according to the third aspect of the present invention, since a plurality of the treatment chambers, which are connected in series, are arranged in parallel rows, it is possible to treat a large number of to-be-treated automobiles.

According to the automobile high-temperature pest extermination device according to the fourth aspect of the present invention, since a centralized management part for collectively managing the operations of the plurality of treatment chambers is included, it is possible to properly perform high-temperature treatment on a large number of to-be-treated automobiles, simplifying the management of the high-temperature treatment and improving treatment efficiency.

BRIEF DESCRIPTION OF DRAWINGS

FIG. 5 is a graph of changes in heating temperatures during high-temperature treatments.

DESCRIPTION OF EMBODIMENTS

Figure 1:
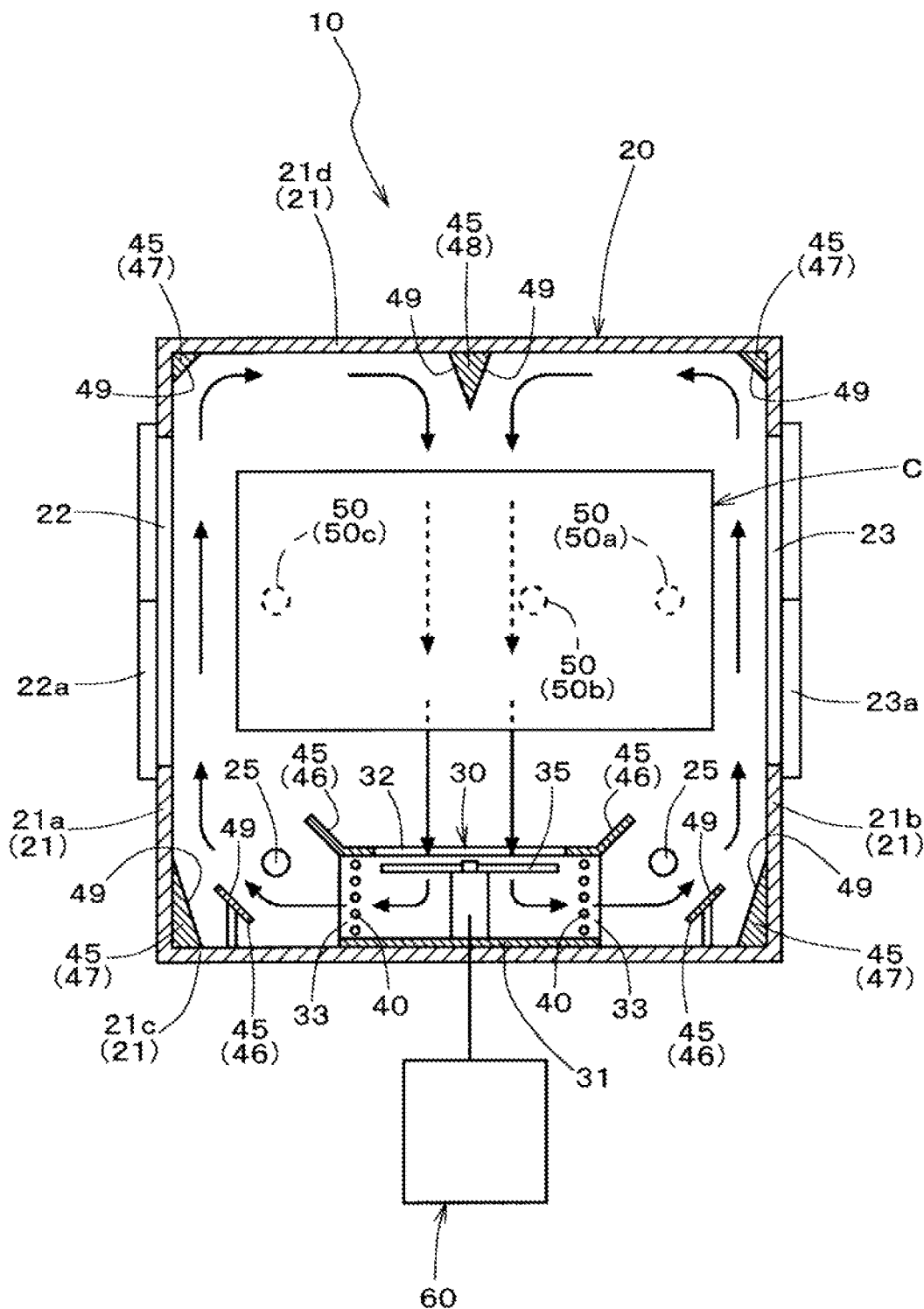
FIG. 1 is a schematic cross-sectional view of an automobile high-temperature pest extermination device according to an embodiment of the present invention.

FIG. 1 shows an automobile high-temperature pest extermination device 10 according to an embodiment of the present invention, comprising a treatment chamber 20, a circulation fan device 30, heating members 40, and rectification members 45. Reference sign C represents a to-be-treated automobile, reference numeral 25 represents chamber interior temperature detection means of the treatment chamber, reference numeral 50 represents vehicle interior temperature detection means of the to-be-treated automobile C, and reference numeral 60 represents heating temperature control means. The high-temperature pest extermination device 10 is a device for exterminating pests attached to the interior or exterior of a to-be-treated automobile C, which is a conventional automobile such as a passenger car or truck, by a high-temperature treatment. The to-be-treated automobile C is, in particular, an automobile for export. The high-temperature pest extermination device 10 is mounted in a facility, such as a quarantine inspection facility or the like, at the port at which loading of automobiles for export is carried out. Target pests for extermination include insects such as stink bugs, cockroaches, weevils, moths, grasshoppers, flies, aphids, and includes larvae and eggs in addition to adult insects.

As shown in FIG. 1, the treatment chamber 20 an enclosed space into and from which a to-be-treated automobile C can be received and discharged and in which the high-temperature treatment can be performed on the to-be-treated automobile C received therein. The treatment chamber 20 is composed of a ceiling, floor, and side wall, each of which is made of a wall material having heat resistance and thermal insulation properties. An inlet 22 and an outlet 23 for receiving and discharging the to-be-treated automobile C, respectively, are formed in the side wall 21. The inlet 22 and the outlet 23 are arranged opposite each other and the to-be-treated automobile C can pass straight through the chamber from the inlet 22 to the outlet 23. Furthermore, the inlet 22 and the outlet 23 may be formed by the same opening through which the to-be-treated automobile C, which is advanced (or reversed), can be loaded into the treatment chamber 20, and the to-be-treated automobile C, which is reversed (or advanced), can be discharged from the treatment chamber 20. The loading of the to-be-treated automobile C into the treatment chamber 20 is performed by means of self-propulsion. In FIG. 1, reference numeral 21a represents a first side wall part in which the inlet 22 is provided, 21b represents a second side wall part facing opposite the first side wall part 21a, 21c represents a third side wall part on which a circulation fan device 30, which is described later, is arranged, and 21d represents a fourth side wall part facing opposite the third side wall part 21c. Reference numeral 22a represents a loading door part for opening and closing the inlet 22 and 23a represents a discharge door part for opening and closing the outlet 23.

As shown in FIG. 1, a chamber interior temperature detection means 25 for detecting the temperature inside the chamber is arranged in the treatment chamber 20. Any known temperature sensor can be used as the chamber interior temperature detection means 25. The chamber interior temperature detection means 25 is preferably mounted in an area in which the temperature is high as compared to the other areas in the treatment chamber 20. The installation location of the chamber interior temperature detection means 25 is, for example, in the vicinity of the discharge parts 33 of the circulation fan device 30, which is described later and which corresponds to a heated air generation source. Thus, by performing temperature detection in areas in which the temperature is high as compared to other areas, it can be assumed that the temperature inside t the treatment chamber 20 as a whole is not higher than the temperature detected by the chamber interior temperature detection means 25. Furthermore, the temperature inside the chamber can be more accurately estimated by mounting chamber interior temperature detection means 25 in several locations within the treatment chamber 20.

Figure 2:
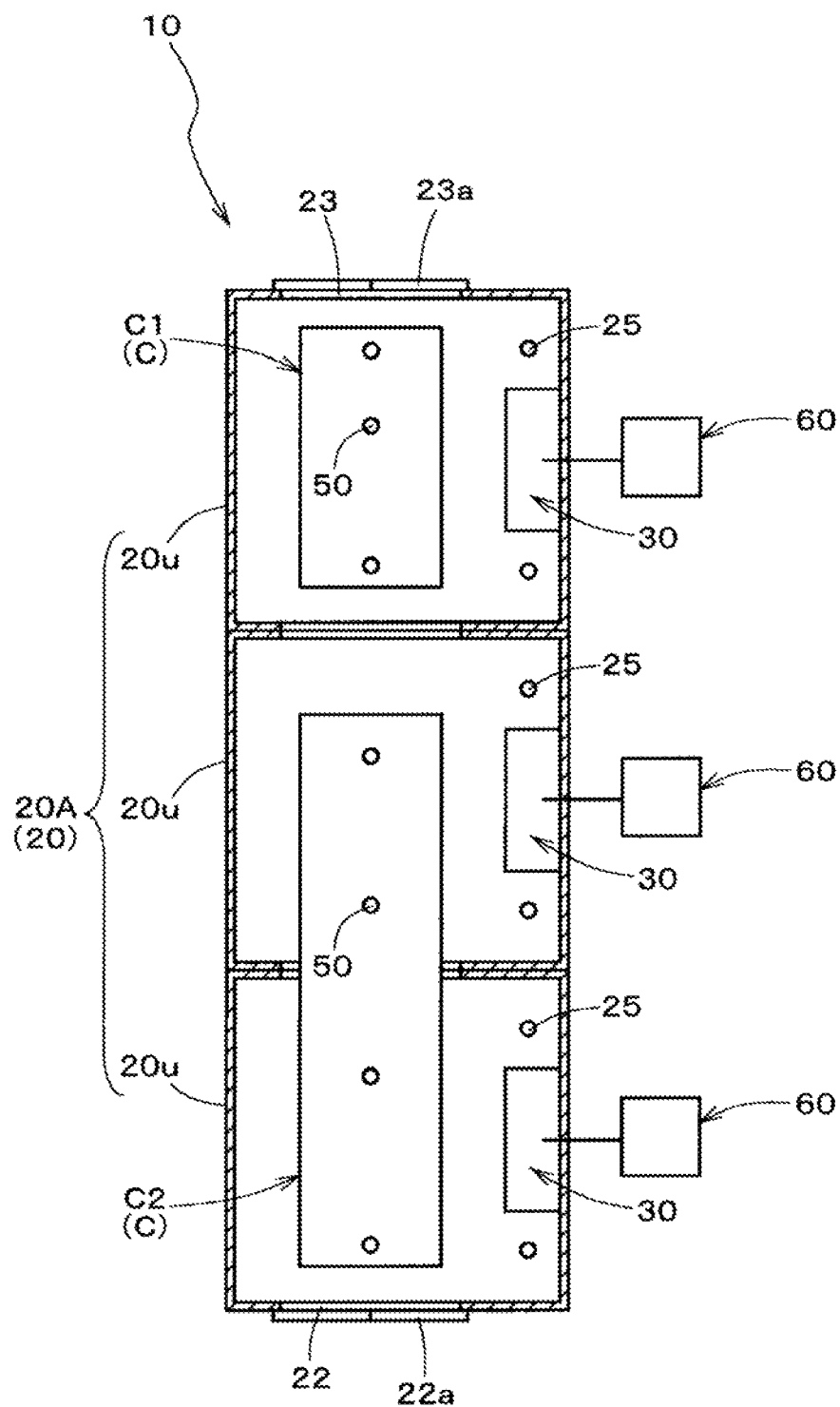
FIG. 2 is a schematic view of a high-temperature pest extermination device in which a plurality of treatment chambers are connected.

The size of the treatment chamber 20 can be appropriately selected in accordance with the size of the to-be-treated automobile C, the number of to-be-treaded automobiles to be treated, the size of the installation location, treatment efficiency, etc. Furthermore, as shown in FIG. 2, the treatment chamber 20 may be capable of accommodating a plurality of to-be-treated automobiles C, C by connecting a plurality of connectable units 20u, 20u, 20u in series (20 A). In the illustrated example, the treatment chamber 20A, in which three units 20u, 20u, 20u are connected, houses a to-be-treated automobile C1, such as an ordinary passenger car, and a to-be-treated automobile C2 which is larger than the to-be-treated automobile C1, such as a bus. In the treatment chamber 20A, a large to-be-treated automobile C2 is housed in a plurality (two in the illustrated example) of units 20u, 20u. In other words, it is not necessary that a single unit 20u correspond to a single to-be-treated automobile C. Rather, housing can be performed in any way as long as the to-be-treated automobile can be housed within the connected treatment chamber 20A. Therefore, by connecting a plurality of treatment chambers (20u, 20u, 20u), the housing space for the to-be-treated automobiles C within the treatment chamber 20 can be freely adjusted. Thus, adaptation to the number of to-be-treated automobiles C and the size of the installation location becomes easy, whereby versatility is improved. Note that in the illustrated example, the units 20u, 20u are connected via the side wall parts. However, the side wall parts may be configured to be detachable, such that the units 20u, 20u may be directly connected to each other at the time of connection without being connected via the side wall parts.

Figure 3:
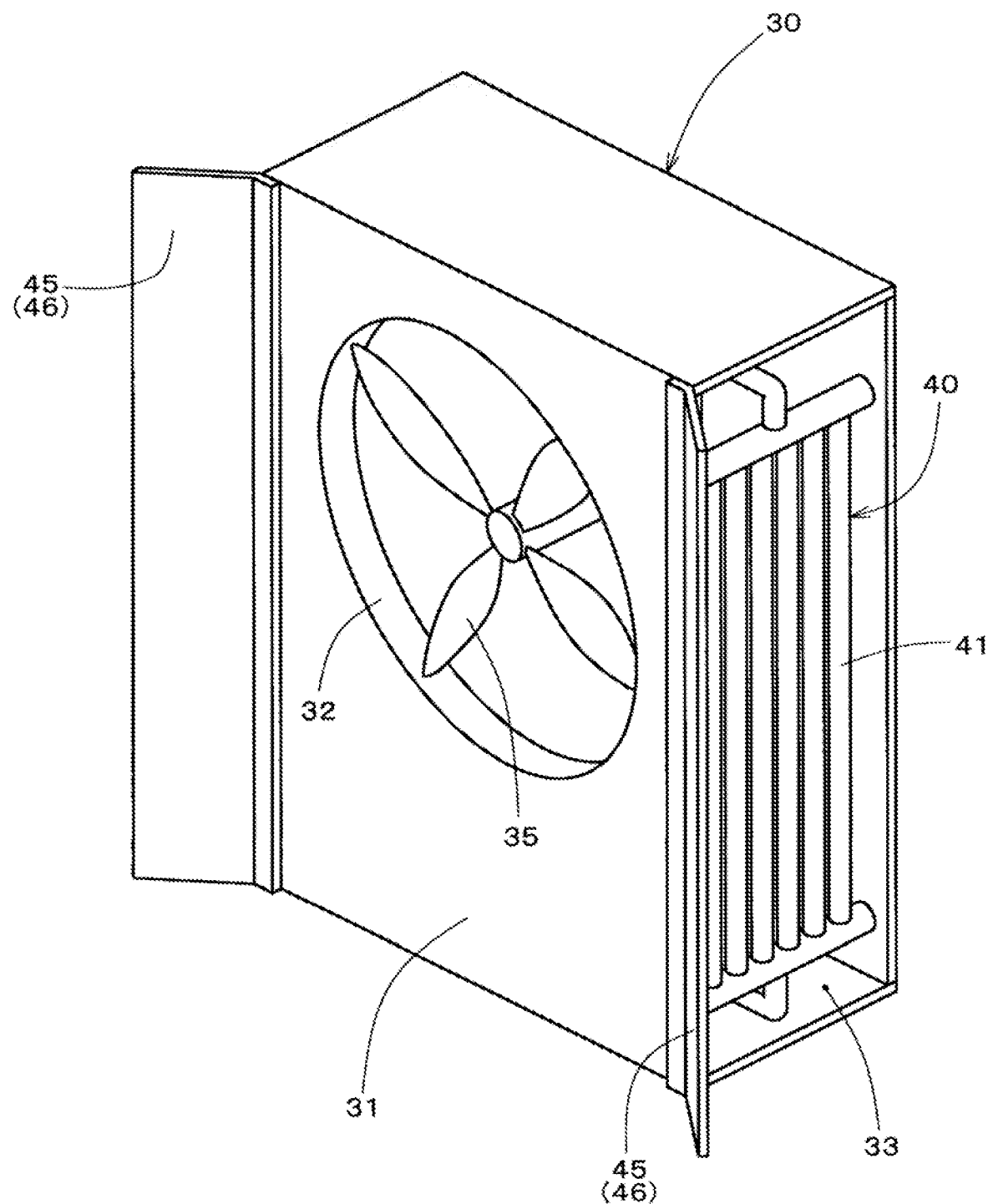
FIG. 3 is a perspective view of a circulation fan device.

As shown in FIG. 1, the circulation fan device 30 is arranged inside the treatment chamber 20, circulates and distributes heated air in the treatment chamber 20, and operates to prevent unevenness in the heating of the chamber to maintain a substantially uniform heating temperature. As shown in FIGS. 1 and 3, the embodied circulation fan device 30 comprises a suction part 32, a discharge part 33, and a large propeller fan 35, which is a fan member. In the drawings, reference numeral 31 represents the housing member of the circulation fan device 30. The circulation fan device 30 is arranged on the side wall part 21 (the third side wall part 21c) of the treatment chamber 30 so that the suction part 32 formed on the front surface side of the housing member 31 faces towards the interior of the treatment chamber.

As shown in FIGS. 1 and 3, the fan member 35 is in the form of a suction fan which is arranged so that the front surface side thereof faces the interior of the treatment chamber 20 and which suctions air inside the treatment chamber 20 via the suction part 35. The form of the fan member 35 may appropriately have two blades, three blades, four blades, or the like. The size of the fan member 35 may be appropriately selected in accordance with the size of the treatment chamber 20, heating efficiency, etc., and in the present embodiment, the fan member 35 is large-sized, having a diameter of, for example, about 1000 mm to 1500 mm. One or a plurality (one in the illustrated example) of fan members 35 may be provided in accordance with the size of the treatment chamber.

The heating member 40 is a member for heating the air suctioned by the fan member 35. Heating members 40 are arranged in the discharge parts 33, which are described later. Any known heating device such as a heat exchanger, such as steam piping or hot water piping, or an electric wire heater, may be used as the heating member 40. The heating member 40 shown in FIG. 3 is a steam piping-type heat exchanger in which a plurality of straight tubular piping members 41 are arranged in parallel to allow steam to flow through each piping member 41. Since a plurality of piping members 41 are formed in a straight pipe shape and arranged in parallel, the occurrence of temperature unevenness upon heating is suppressed, whereby thermal efficiency is improved.

As shown in FIGS. 1 and 3, the discharge parts 33 are opening parts for ventilation which are formed by fully opening both side portions of the housing member 31 of the circulation fan device 30. The heated air which is suctioned by the fan member 35 and heated by the heating members 40 is discharged from the treatment chamber 20 through the discharge parts 33. Furthermore, rectification members 45 for adjusting the flow direction of the heated air discharged into the chamber are provided in the discharge parts 33. The rectification members 45 are wind direction restriction parts 46 which are provided on both ends of the front of the housing member 31 and which are formed of plate-shaped members which are bent and extend from the end parts toward the front side. The rectification members 45 formed from the wind direction restriction parts also serve as guides for discharging the heated air from the discharge parts 33 in a straight forward direction without diffusing and for allowing the air in the chamber to flow into the suction part 32. Note that, though not illustrated, discharge fan members may be arranged in the discharge parts 33 as necessary. By arranging discharge fan members in the discharge parts 33, the discharge of heated air can be further promoted.

As shown in FIG. 1, since the circulation fan device 30 described above is arranged so that the front surface side of the fan member 35 faces the interior of the treatment chamber 20, heated air is circulated in the horizontal directions in the treatment chamber 20. In particular, first, air in the treatment chamber 20 is suctioned by the fan member 35 from the suction part 32 on the front side of the circulation fan device 30. This suctioned air is discharged toward both sides of the circulation fan device 30 via the discharge parts 33 on the rear side of the fan member 35. At this time, the air is heated while passing through the heating members 40 arranged in the discharge parts 33, and the heated air is discharged from the interior of the treatment chamber 20 through the discharge parts 33. The heated air discharged from the discharge parts 33 circulates along the walls of the chamber 20.

The air volume and air speed of the fan member 35 of the circulation fan device 30 will be described. Since the fan member 35 of the present embodiment is a large-sized propeller fan having a diameter of about 1000 mm to 1500 mm, the air volume thereof is 1500 m$^3$ per minute, and the average air speed is 5.8 m per second, a degree at which the leaves and branches of a tree would shake (wind power 2). The treatment chamber of the present embodiment, in the case of a large chamber, has a volume of 391 m$^3$, and in the case of a small chamber, has a volume of 346 m$^3$. In accordance with experimentation, an air speed of heated air of 4 to 7 m/sec (wind power 2 to 3) is preferred, since the heat treatment can be efficiently performed at such an air speed. In the present embodiment, since the efficiency of raising and maintaining the heat treatment temperature (60 to 80° C.) is good, the treatment time can be drastically reduced (the entire process takes about 30 minutes).

Next, the circulation and distribution of heated air within the heating chamber will be described. Heated air discharged from the discharge parts 33 circulates along the side walls of the treatment chamber 20, as described above. The heated air circulating in the direction of the first side wall part 21a of FIG. 1 then circulates in the direction of the fourth side wall part 21d along the first side wall part 21a. Further, heated air circulating in the direction of the second side wall part 21b then circulates in the direction of the fourth side wall part 21d along the second side wall part 21b bilaterally symmetrically with the heated air circulating in the direction of the first side wall part 21b. The first side wall part 21a side heated air and the second side wall part 21b side heated air combine in the central part of the fourth side wall part 21d, circulate in the central direction of the treatment chamber 20, and are suctioned by the fan member 35 of the circulation fan device 30 toward the circulation fan device 30.

Thus, the circulation fan device 30 creates a flow of air from the third side wall part 21c to the fourth side wall part 21d along the side wall part 21 of the treatment chamber 20 by suctioning air inside the treatment chamber through the suction part 32 on the front side of the circulation fan device 30 by the fan member 35 and discharging the air as heated air from the discharge parts 33 on both sides. Further, since the heated air circulated on the fourth side wall part 21d side is again suctioned by the fan member 35, the heated air in the treatment chamber 20 is circulated. Since the discharge parts 33 are formed by fully opening the side parts of the circulation fan device 30, the discharged heated air is circulated in the treatment chamber 20 in the substantially horizontal directions.

When the heated air is circulated by the circulation fan device 30, as shown in FIG. 1, rectification members 45 for adjusting, in the horizontal direction, the flow direction of the heated air are arranged in various locations within the treatment chamber 20. The rectification members 45 each include a wind receiving surface 49 angled in a predetermined direction with respect to the flow direction of the heated air. The wind receiving surfaces 49 guide the flow direction in the direction of inclination when the heated air collides with the wind receiving surfaces 49 of the rectification members 45. The rectification members 45 of the present embodiment include wind direction auxiliary parts 47 arranged in the corners of the treatment chamber 20, and a wind direction auxiliary part 48 arranged in the vicinity of the junction of the heated air from the first side wall part 21a side and the heated air from the second side wall part 21b side, as well as wind direction restriction parts 46 consisting of plate-like members disposed in the vicinity of the discharge parts 33 of the circulation fan device 30. The heated air discharged from the circulation fan device 30 can be more efficiently circulated and distributed in the horizontal direction within the treatment chamber by providing the wind direction restriction parts 46 and the wind direction auxiliary parts 47, 48 of the rectification members 45, and the heated air can be effectively brought into contact with the interior and exterior of a box-type automobile including a floor plate, a roof plate, and an intricate internal structure.

Next, as shown in FIG. 1, vehicle interior temperature detection means 50 are members which are mounted inside the to-be-treated automobiles C and which detect the vehicle interior temperature. A known temperature sensor is used as the vehicle interior temperature detection means 50. Vehicle interior temperature detection means 50 are appropriately mounted in a position which is relatively resistant to heating or a position which is relatively easily heated. Positions which are relatively resistant to heating include the interior of the engine compartment, under the seats, etc., of the to-be-treated automobile C, and are positions (low-temperature positions) at which the temperature tends to be lowest compared with other positions within the to-be-treated automobile C at the time of high-temperature treatment. Furthermore, positions which are relatively easily heated include on the seat, etc., of the to-be-treated automobile C, and are positions (high-temperature positions) at which the temperature tends to be highest as compared to the other positions within the to-be-treated automobile C at the time of high-temperature treatment.

By detecting the temperature at positions (low-temperature positions) at which the temperature tends to be lowest compared with other positions within the to-be-treated automobile C using the vehicle interior temperature detection means 50, it is possible to assume that the vehicle interior temperature of the to-be-treated automobile C as a whole is not less than the temperature detected by the vehicle interior temperature detection means 50. Furthermore, by detecting the temperature at positions (high-temperature positions) which are easily heated as compared with other positions within the to-be-treated automobile C using the vehicle interior temperature detection means 50, it is possible to assume that the vehicle interior temperature of the to-be-treated automobile 50 as a whole is not less than the temperature detected by the vehicle interior temperature detection means 50. By mounting vehicle interior temperature detection means 50 in both the positions (low-temperature positions) which are resistant to heating and the positions (high-temperature positions) which are easily heated and detecting the temperatures thereof, it is possible to assume that the vehicle interior temperature of the to-be-treated automobile C as a whole is not less than the temperature detected at the low-temperature positions and not greater than the temperature detected at the high-temperature positions. Note that vehicle interior temperature detection means 50 are preferably arranged in several locations within the to-be-treated automobile C. By detecting the vehicle interior temperatures at several locations, the vehicle interior temperature of the to-be-treated automobile C can be more accurately estimated.

As shown in FIG. 1, the heating temperature control means 60 is mounted outside the treatment chamber 20 and controls the heating temperature of the circulation fan device 30 based on the vehicle interior temperature detection means 50. Any known control device can be used as the heating temperature control means 60. Insects such as stink bugs, which are extermination target pests, are weak against high temperatures. Such insects are killed by exposure to high temperatures of, for example, 50° C. or higher. It is thought that the proteins within the body of the pests solidify due to the high temperatures. However, the to-be-treated automobiles C are precision machinery and utilize members made of resins in various places. Thus, exposure to high temperatures for long periods adversely affects various equipment and members, etc., which may cause damage such as breakdown, damage, or deterioration. In order to avoid adverse effects on the to-be-treated automobiles C due to the high temperatures, the heating treatment is set to 80° C. or less. The heating temperature control means 60 controls so as to restrict the vehicle interior temperature of the to-be-treated automobile C detected by the vehicle interior temperature detection means 50 to 50 to 80° C., more preferably 60 to 75° C. Control of the circulation fan device 30 is performed by adjusting the rotation speed of the fan member 35, the amount of steam provided to the circulation fan device 30, etc.

The heating temperature control means 60 controls the heating temperature of the circulation fan device 30 based on the chamber interior temperature detection means 25 along with the control of the circulation fan device 30 based on the vehicle interior temperature detection means 50. The chamber interior temperature detected by the chamber interior temperature detection means 25 is estimated to be the highest temperature within the treatment chamber 20, and thus corresponds to the temperature upper limit of the chamber interior temperature. Further, the chamber interior temperature corresponds to the vehicle exterior temperature of the to-be-treated automobile C, and thus impacts pest extermination of the exterior of the to-be-treated automobile C, damage due to the high temperature, or the like. Thus, in the same manner as the vehicle interior temperature, the heating temperature control means 60 control so as to restrict the chamber interior temperature (the vehicle exterior temperature of the to-be-treated automobile C) within the treatment chamber detected by the chamber interior temperature detection means 25 to 50 to 80° C. or less, more preferably 60 to 75° C. Note that in the case of the treatment chamber 20A, in which a plurality of units 20u are connected, since it is necessary to manage the chamber interior temperature as the entire treatment chamber 20A (all units), it is preferable to collectively control the detection temperature based on the chamber interior temperature detection means of each unit 20u.

Control of the treatment duration of the high-temperature treatment is performed by the heating temperature control means 60. The treatment duration of the high-temperature treatment is set in accordance with the size or the number of the to-be-treated automobiles C, etc., and is, for example, about 10 to 20 minutes after the vehicle interior temperature of the to-be-treated automobile C reaches a predetermined temperature. By selected this treatment duration, extermination target pests can be reliably killed, and treatment efficiency and cost are also preferable. In the present embodiment, since the efficiency of raising and maintaining the heat treatment temperature (60 to 80° C.) is high, as described above, the overall treatment duration can be shortened to about 30 minutes.

Figure 4:
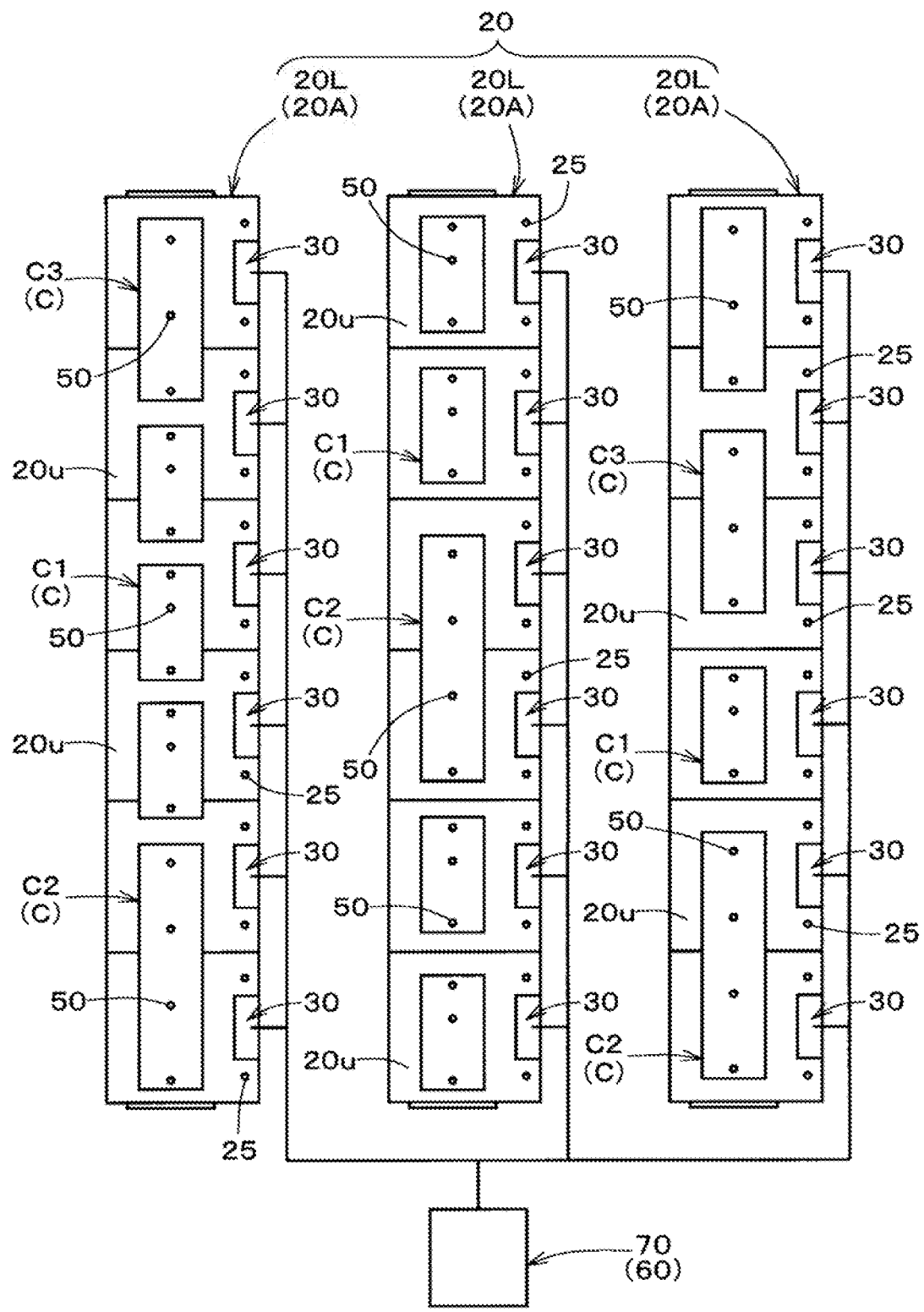
FIG. 4 is a schematic view of a high-temperature pest extermination device in which a plurality of treatment chambers are arranged in parallel rows.

In the high-temperature pest extermination device 10 of the present invention, as shown in FIG. 4, a plurality of treatment chambers are arranged in parallel rows (20L, 20L, 20L), whereby high-temperature treatment can be performed on a plurality of to-be-treated automobiles C. The plurality of treatment chambers arranged in parallel rows 20L, 20L, 20L may be composed of a plurality of connectable units 20u connected in series (treatment chamber 20A). The illustrated example includes three rows of treatment chambers 20L, 20L, 20L each composed of a treatment chamber 20A in which six units 20u are connected in a single row. Each row of the treatment chambers 20L, 20L, 20L irregularly houses a small to-be-treated automobile C1, a large to-be-treated automobile C2, and a medium to-be-treated automobile C3. By arranged a plurality of connected treatment chambers 20A in parallel rows, high-temperature treatment can be performed on a larger number of to-be-treated automobiles, whereby treatment efficiency can be increased.

Furthermore, the high-temperature pest extermination device 10, in which a plurality of treatment chambers are arranged in parallel rows, preferably includes a centralized management part 70 for collectively managing the high temperature treatment by the circulation fan devices 30 of each of the treatment chambers 20L, 20L, 20L. Any known controller can be used as the centralized management part 70. The centralized management part 70 controls each corresponding circulation fan device 30 based on the vehicle interior temperature detection means 50 of each of the plurality of treatment chambers 20. In particular, when a treatment chamber 20A in which a plurality of units 20u are connected is included, each circulation fan device 30 is preferably controlled based on the chamber interior temperature detection means 25 and vehicle interior temperature detection means 50. This is because treatment at a chamber interior temperature which is managed for the treatment chamber 20A as a whole in which the units are connected, is more advantageous in terms of efficiency than managing the temperature upper limit of the high-temperature treatment for each of the plurality of to-be-treated automobiles C. Note that the centralized management part 70 may be configured to serve as the heating temperature control means 60 and heating temperature control means 60 may be additionally provided to control each high-temperature treatment based on each heating temperature control means 60. The centralized management part 70 makes it possible to easily assess the overall situation of the high-temperature treatment for a large number of to-be-treated automobiles C and to efficiently respond to the treatment situation.

Next, the automobile high-temperature pest extermination method using the high-temperature pest extermination device 10 of the present invention will be described. As shown in FIG. 1, the high-temperature pest extermination method includes loading a to-be-treated automobile C into the treatment chamber 20, heating the treatment chamber 20, detecting the vehicle interior temperature by the vehicle interior temperature detection means 50 mounted inside the to-be-treated automobile C, controlling the heating temperature by the heating temperature control means 60 based on the vehicle interior temperature detection means 50, and performing the high-temperature treatment on the to-be-treated automobile C at a temperature higher than a predetermined temperature, whereby pests inside the to-be-treated automobile C are exterminated. An example of the high-temperature pest extermination method in which a single to-be-treated automobile C is treated in a single treatment chamber 20 will be described in detail below.

First, a necessary number of vehicle interior temperature detection means 50 are arranged, in advance, in positions which are relatively resistant to heating, such as under the seat or within the engine compartment of the to-be-treated automobile C. In the example illustrated in FIG. 1, an engine compartment vehicle interior temperature detection means 50a, an under-seat vehicle interior temperature detection means 50b, and a trunk compartment vehicle interior temperature detection means 50c are arranged. Furthermore, the temperature conditions and treatment duration of the high-temperature treatment by the circulation fan device 30 are set by the heating temperature control means 60. The conditions of the high-temperature treatment include a temperature upper limit of 75° C., a treatment temperature of 60° C., and a treatment duration of 10 minutes.

After the high-temperature treatment has been set, the to-be-treated automobile C is loaded into the treatment chamber 20 by self-propulsion. The doors, hood, trunk lid, etc., of the to-be-treated automobile C loaded into the treatment chamber 20 are opened to allow air to flow into the passenger compartment, the engine compartment, the trunk, etc. Subsequently, the inlet 22 of the treatment chamber 20 is closed, closing the interior of the chamber, and heating in the treatment chamber 20 by the circulation fan device 30 is started. The circulation fan device 30 circulates heated air in the horizontal directions of the treatment chamber 20 by the fan member 35.

In particular, air inside the treatment chamber 20 is suctioned by the fan member 35 through the front of the circulation fan device 30, and the suctioned air is heated by the heating members 40 within the housing member 31. The air heated in this way is discharged as heated air into the treatment chamber 20 from the discharge parts 33 on both sides of the circulation fan device 30. At this time, since the discharge parts 33 are formed by opening the entirety of the sides of the circulation fan device 30, the discharged heated air circulates through the treatment chamber 20 in the horizontal directions. The heated air discharged from the sides of the circulation fan device 30 circulates from the third side wall part 21c side to the fourth side wall part 21d side along the side wall parts of the first side wall part 21a side and the second side wall part 21b side. Further, the heated air on both sides collides in the central part of the fourth side wall part 21d, circulates in the central direction of the treatment chamber 20, and is suctioned into the circulation fan device 30 by the fan member 35 of the circulation fan device 30. Thus, the circulation of the heated air in the horizontal directions along both the left and right side wall parts 21 within the treatment chamber 20 is repeated. As a result, the interior of the treatment chamber 20 can be efficiently heated.

In the heating by the circulation fan device 30, the interior of the treatment chamber 20 is entirely heated so that the interior of the to-be-treated automobile C loaded into the treatment chamber 20 is gradually heated. The graph of FIG. 5 shows the temperature change by the circulation fan device 30. In the graph of FIG. 5, the temperature changes of the chamber interior temperature (vehicle external temperature) detected by the chamber interior temperature detection means 25, a first vehicle interior temperature detected by the engine compartment vehicle interior temperature detection means 50a, a second vehicle interior temperature detected by the under-seat vehicle interior temperature detection means 50b, and a third vehicle interior temperature detected by the trunk vehicle interior temperature detection means 50c are shown.

As shown in FIG. 5, as the chamber interior temperature (refer to reference numeral 25) rises, the vehicle interior temperatures rise (reference numerals 50a, 50b, 50c). Operation of the circulation fan device 30 is controlled by the heating temperature control means 60 so that the chamber interior temperature is maintained at the temperature upper limit (75° C. in this example) based on the chamber interior temperature detected by the chamber interior temperature detection means 25. This is a measure to prevent damage or the like from occurring in the to-be-treated automobile C when the chamber interior temperature is higher than 80° C.

As shown in FIG. 5, the vehicle interior temperature rises over time as the temperature of the exterior of the vehicle rises. By maintaining the chamber interior temperature at the temperature upper limit (75° C.), the increased vehicle interior temperature can reach the treatment temperature (60° C. in this example) of the high-temperature treatment. The change in the vehicle interior temperature differs depending on the position in the to-be-treated automobile C. Thus, the time to reach the treatment temperature (60° C.) of the high-temperature treatment also is not the same for each position. In the example shown in FIG. 5, the vehicle interior temperature (50c) of the trunk first reaches the treatment temperature, and then the engine compartment vehicle interior temperature (50a) and the under-seat vehicle interior temperature (50b) reach the treatment temperature in this order. Among the plurality of vehicle interior temperature detection means (50a, 50b, 50c), the time (t) at which the temperature reaches the treatment temperature (60° C.) last is defined as the high-temperature treatment start time.

The position which reaches the treatment temperature last is presumed to be the position within the to-be-treated automobile C at which the temperature is lowest. Thus, when this position reaches the treatment temperature, it can be considered that the entire to-be-treated automobile C has reached the treatment temperature or higher and the entire to-be-treated automobile C is in a state in which the high-temperature treatment can be appropriately performed. Thus, by using this time (t) as the high-temperature treatment start time, the to-be-treated automobile C can be subjected to the high-temperature treatment without issue.

The high-temperature treatment is maintained in a high-temperature state at the treatment temperature (60° C.) or higher from the start time (t) until the set duration (10 minutes in this example) has elapsed. During the high-temperature treatment, the chamber interior temperature is maintained at the temperature upper limit (75° C.). As a result, the vehicle interior temperature of the to-be-treated automobile C rises within the range of the chamber interior temperature (75° C.) or less even after reaching the treatment temperature (60° C.). Thus, the vehicle interior temperature does not reach a high temperature greater than 80° C., whereby adverse effects on the to-be-treated automobile C due to the high temperature can be prevented. During the high-temperature treatment (10 minutes), the vehicle interior temperature and the vehicle exterior temperature (chamber interior temperature) are continuously maintained at 50° C. (60° C. in this example) or higher, a temperature at which pests are killed. Thus, pests adhering to the to-be-treated automobile C can be reliably exterminated.

After the treatment duration (t+10 minutes) of the high-temperature treatment has elapsed, the circulation fan device 30 stops and the inlet 22 and outlet 23 of the treatment chamber 20 open, whereby the to-be-treated automobile C is gradually cooled. After gradual cooling of the to-be-treated automobile C has been carried out as necessary, a new untreated to-be-treated automobile C is loaded, and the same process is then repeated.

Next, a high-temperature pest extermination method in which a high-temperature pest extermination device 10 in which a plurality of connected treatment chambers 20 are arranged in a plurality of rows is used will be described. As shown in FIG. 4, in this high-temperature pest extermination method, a plurality of to-be-treated automobiles C in which vehicle interior temperature detection means 50 have been appropriately arranged are appropriately loaded into the treatment chambers 20L, 20L, 20L. After the necessary number of loadings has been completed, the treatment chambers 20L, 20L, 20L are closed. Thereafter, heating by the circulation fan devices 30 of the respective treatment chambers 20 is started by the control of the centralized management part 70.

The centralized management part 70 controls the operation of each of the circulation fan devices 30 so as to maintain all of the chamber interior temperatures at the temperature upper limit (75° C.) or less based on the chamber interior temperature detected by the chamber interior temperature detection means 25 of each treatment chamber 20. Furthermore, the vehicle interior temperatures of the to-be-treated automobiles C rise over time as the chamber interior temperatures rise. The centralized management part 70 performs control of the circulation fan devices 30 of the plurality of treatment chambers arranged in parallel rows 20L, 20L, 20L based on the vehicle interior temperature detection means 50 for each row. In other words, each treatment chamber 20L, 20L, 20L is controlled so that high-temperature treatment is performed from the time any of the plurality of vehicle interior temperature detection means 50 last reaches the treatment temperature (60° C.) until the set treatment duration (10 minutes) has elapsed.

In each row, gradual cooling of the to-be-treated automobile C is sequentially performed from the treatment chamber 20 L in the row in which the treatment duration of high-temperature treatment has elapsed, and the replacement with new untreated to-be-treated automobiles C is performed. Thereafter, the same steps are repeated. Thus, when the high-temperature treatments by each of the circulation fan devices 30 of the plurality of treatment chambers arranged in parallel rows 20L, 20L, 20L are collectively managed by the centralized management part 70, high-temperature treatment can be appropriately performed for more to-be-treated automobiles C and management of a plurality of high-temperature treatments is simplified, whereby treatment efficiency is improved.

As illustrated and described above, since the automobile high-temperature pest extermination device of the present invention includes a circulation fan device arranged in the treatment chamber in which the to-be-treated automobile is housed, the suction part of which is oriented toward the inside of the treatment chamber, heating members mounted in the discharge parts of the circulation fan device, and a rectification member for adjusting the flow direction of the heated air delivered into the chamber via the heating members, automobile pests can be reliably controlled by the high-temperature treatment without the use of a fumigation agent. Additionally, according to the present invention, by providing a circulation fan device and heating members in the treatment chamber to circulate and distribute heated air, heating unevenness within the chamber is controlled, whereby the treatment chamber can be effectively and efficiently heated while maintaining a substantially uniform heating temperature, and as a result, treatment efficiency can be significantly improved and cost can be reduced. Furthermore, since the fan member, which is a large propeller fan, is arranged so that the front surface side thereof faces the interior of the treatment chamber in the present invention, the air within the chamber can be drawn and discharged at an appropriate air volume and speed. Even in the case of automobiles, which are large treatment targets, the heat treatment temperature can be raised and maintained efficiently, whereby effective heat treatment can be performed and treatment time can be greatly reduced. Due to the rectification member, which adjusts, in the horizontal direction, the flow direction of the heated air delivered into the chamber through the heating members, the heated air can be effectively brought into contact with the interior and exterior of a box-shaped automobile having a floor plate, a roof plate, and an intricate internal structure, and appropriate pest control can be achieved even for a large number of to-be-treated automobiles, whereby appropriate pest control can be performed more efficiently and effectively even for a large number of to-be-treated automobiles.

INDUSTRIAL APPLICABILITY

Since the automobile high-temperature pest extermination device of the present invention comprises a circulation fan device and a heating member within the treatment chamber and the heated air is circulated and distributed, even in large treatment spaces for automobiles, in addition to efficient high-temperature treatment, as described in the Examples, by connecting a plurality of treatment chambers, thermal treatment of a large number of different types of to-be-treated automobiles can be efficiently performed, and adaptation to mass treatment and the size of the installation location becomes easy, whereby versatility is improved and high industrial applicability is achieved. The automobile high-temperature pest extermination device of the present invention has significant actual and practical advantages in, for example, the treatment of pests on exported automobiles in harbors, in which there are many restrictions on the installation of treatment facilities.

REFERENCE SIGNS LIST 10 automobile high-temperature pest extermination device
20 treatment chamber
20A plurality of connected treatment chambers
20L plurality of treatment chambers arranged in parallel
20u unit 21 side wall part
21a first side wall part
21b second side wall part
21c third side wall part
21d fourth side wall part
22 inlet
22a loading door part
23 outlet
23a discharge door part
25 chamber interior temperature detection means
30 circulation fan device
31 housing member
32 suction part
33 discharge part
35 fan member
40 heating member
41 piping member
45 rectification member
46 rectification member wind direction restriction part
47, 48 rectification member wind direction auxiliary part
49 rectification member wind receiving surface
50, 50a, 5b, 5c vehicle interior temperature detection means
60 heating temperature control means
70 centralized management part
C, C1, C2, C3 to-be-treated automobile
t high-temperature treatment start time

The invention claimed is:

1. An automobile high-temperature pest extermination device, comprising:
   at least one treatment chamber including an inlet and an outlet, which comprise openable and closable door parts, in which heated air which has been heated to a pest extermination temperature is applied to an enclosed space in which a to-be-treated automobile is self-propelled into and accommodated therein,
   a circulation fan device arranged in the at least one treatment chamber and including all of a suction part, discharge parts, and a fan member arranged in a housing member, the fan member comprising a propeller fan having a diameter in a range of 1000 mm to 1500 mm and a front side of the fan member being oriented toward an inside of the at least one treatment chamber, the circulation fan device being configured so that air in the at least one treatment chamber is suctioned from the front side thereof via the suction part, and the suctioned air is discharged in both side directions via the discharge parts on a rear surface of the fan member, the discharge parts being opening parts formed by fully opening side portions of the housing member,
   a heating member provided in the discharge parts of the circulation fan device to heat discharged air, the heating member being fully contained within the housing member of the circulation fan device,
   a rectification member for adjusting, in a horizontal direction, a flow direction of the heated air delivered into the at least one treatment chamber via the heating member,
   a chamber interior temperature detection means for detecting a chamber interior temperature of the at least one treatment chamber,
   a vehicle interior temperature detection means for detecting a vehicle interior temperature of the to-be-treated automobile, and
   a heating temperature control means for controlling a heating temperature of air exiting the circulation fan device and a treatment time based on the chamber interior temperature detection means and the vehicle interior temperature detection means.

2. The automobile high-temperature pest extermination device according to claim 1, wherein the at least one treatment chamber further comprises a plurality of treatment chambers connected in series as a connectable treatment unit so as to house a plurality of to-be-treated automobiles therein.

3. The automobile high-temperature pest extermination device according to claim 2, wherein the plurality of treatment chambers, which are connected in series, are arranged in parallel rows.

4. The automobile high-temperature pest extermination device according to claim 2, comprising a centralized management part for collectively managing operations of the plurality of treatment chambers.

5. The automobile high-temperature pest extermination device according to claim comprising a centralized management part for collectively managing operations of the plurality of treatment chambers.

6. The automobile high-temperature pest extermination device according to claim 1, wherein the at least one treatment chamber has a volume of 346 $m^3$ or more and 391 $m^3$ or less.

7. The automobile high-temperature pest extermination device according to claim 1, wherein the propeller fan has an air volume of 1500 $m^3$ and an air speed of 4 to 7 m per second.

8. The automobile high-temperature pest extermination device according to claim 1, wherein the rectification member further comprises a plurality of rectification members, the rectification members comprising wind direction auxiliary parts respectively arranged in each corner of the at least one treatment chamber and wind direction restriction parts consisting of plate-like members disposed in a vicinity of the discharge parts of the circulation fan device, the rectification members configured to adjust the flow direction of the heated air through the interior of the to-be-treated automobile.

9. The automobile high-temperature pest extermination device according to claim 1, further comprising a transport means for loading the to-be-treated automobile into the at least one treatment chamber.

10. The automobile high-temperature pest extermination device according to claim 1, wherein the vehicle interior temperature detection means are mounted inside the to-be-treated automobile at positions which are resistant to heating or being easily heated.

11. The automobile high-temperature pest extermination device according to claim 1, wherein the heating temperature control means controls the vehicle interior temperature of the to-be-treated automobile to a range of 50 to 80° C. based on the temperature detected by the vehicle interior temperature detection means.

12. The automobile high-temperature pest extermination device according to claim 1, wherein the heating temperature control means controls the chamber interior temperature to a range of 25 to 80° C. based on the temperature detected by the chamber interior temperature detection means.

13. The automobile high-temperature pest extermination device according to claim 1, wherein the heating temperature control means controls the treatment time of the high-temperature in accordance with the size or number of the to-be-treated automobile(s).

* * * * *